US011529097B2

(12) United States Patent
Hickey

(10) Patent No.: US 11,529,097 B2
(45) Date of Patent: Dec. 20, 2022

(54) MICRO-COHERENCE NETWORK STRENGTH AND DEEP BEHAVIOR MODIFICATION OPTIMIZATION APPLICATION

(71) Applicant: Wellness IP, Inc., Boulder, CO (US)

(72) Inventor: Michael Peter Hickey, Boulder, CO (US)

(73) Assignee: Wellness IP, Inc., Boulder, CO (US)

( * ) Notice: Subject to any disclaimer, the term of this patent is extended or adjusted under 35 U.S.C. 154(b) by 0 days.

(21) Appl. No.: 16/694,288

(22) Filed: Nov. 25, 2019

(65) Prior Publication Data
US 2020/0297268 A1 Sep. 24, 2020

Related U.S. Application Data

(60) Provisional application No. 62/770,940, filed on Nov. 23, 2018, provisional application No. 62/770,951, (Continued)

(51) Int. Cl.
*A61B 5/00* (2006.01)
*A61B 5/16* (2006.01)
(Continued)

(52) U.S. Cl.
CPC ............ *A61B 5/486* (2013.01); *A61B 5/0205* (2013.01); *A61B 5/165* (2013.01); *A61B 5/4884* (2013.01);
(Continued)

(58) Field of Classification Search
CPC ....... A61B 5/486; A61B 5/0205; A61B 5/165; A61B 5/4884; A61B 5/7267;
(Continued)

(56) References Cited

U.S. PATENT DOCUMENTS

| 9,993,190 B2 * | 6/2018 | Preminger | A61B 5/16 |
| 2005/0019734 A1 * | 1/2005 | Peled | A61B 5/7264 |
| | | | 434/236 |

(Continued)

FOREIGN PATENT DOCUMENTS

WO  WO-2018081134 A1 * 5/2018 ............. A61B 5/167

OTHER PUBLICATIONS

Anderson et al., "Stress in America TM: Missing the Heath Care Connection", Survey Report, Feb. 7, 2013, American Psychological Association, 64 pages.

*Primary Examiner* — Brian T Gedeon
*Assistant Examiner* — Joshua Andrew Schum-Houck
(74) *Attorney, Agent, or Firm* — Davis Graham & Stubbs LLP

(57) ABSTRACT

A subject's Default Mode Network is accessed through corresponding measurements of the Micro-Coherence Oximetry Network Strength (MCO-S). An associated MCO-S system (100) includes a wearable (102), a user device (112) and a processing platform (123). The wearable (102) collects subject information sufficient to enable monitoring and optimization of the subject's Default Mode Network include sensors such as pulse oximetry instrumentation and EEG electrodes to obtain brainwave data, oxygen saturation data, heart rate variability data, and galvanic skin conductance data. Information from the sensors may be communicated to a user device (112), such as a cell phone or VR headset. The user device (112) communicates with a remote processing platform (123) that may execute artificial intelligence functionality and other logic in connection with assessing the patient's micro-coherence network strength and optimizing behavior modification protocols in relation to attributes and objectives of the subject.

24 Claims, 9 Drawing Sheets

Related U.S. Application Data filed on Nov. 23, 2018, provisional application No. 62/770,887, filed on Nov. 23, 2018.

(51) Int. Cl.
*A61B 5/0533* (2021.01)
*A61B 5/1455* (2006.01)
*A61B 5/369* (2021.01)
*A61B 5/0205* (2006.01)
*A61B 5/024* (2006.01)

(52) U.S. Cl.
CPC .......... *A61B 5/7267* (2013.01); *A61B 5/7278* (2013.01); *A61B 5/02405* (2013.01); *A61B 5/0533* (2013.01); *A61B 5/14551* (2013.01); *A61B 5/369* (2021.01); *A61B 5/6803* (2013.01)

(58) Field of Classification Search
CPC ... A61B 5/7278; A61B 5/369; A61B 5/02405; A61B 5/0533; A61B 5/14551; A61B 5/14542; A61B 5/389; A61B 5/4064; A61B 5/349; A61B 5/05
See application file for complete search history.

(56) References Cited

U.S. PATENT DOCUMENTS

| | | | |
|---|---|---|---|
| 2012/0150545 A1* | 6/2012 | Simon | A61B 5/162 704/270 |
| 2012/0271148 A1* | 10/2012 | Nelson | A61N 1/36139 600/411 |
| 2013/0046206 A1* | 2/2013 | Preminger | G09B 7/02 600/595 |
| 2016/0015289 A1* | 1/2016 | Simon | A61B 5/7275 600/301 |
| 2016/0287937 A1* | 10/2016 | Fitzgerald | A43B 3/0031 |
| 2017/0333666 A1* | 11/2017 | Goldberg | A61B 5/6801 |
| 2018/0193589 A1* | 7/2018 | McLaughlin | G16H 50/30 |

\* cited by examiner

US 11,529,097 B2

MICRO-COHERENCE NETWORK STRENGTH AND DEEP BEHAVIOR MODIFICATION OPTIMIZATION APPLICATION

FIELD OF THE INVENTION

The present invention relates generally to monitoring and optimizing the human nervous system Default Mode Network or Resting State Network. More particularly, the present invention relates to assessing the strength of a subject's Micro-Coherence Oximetry Network Strength (MCO-S), which is associated with the Default Mode Network, and to enabling deep behavior modification optimization so as to achieve any of multiple associated health, wellness and ability benefits.

BACKGROUND OF THE INVENTION

Health care costs are steadily going up with these costs representing about 17% of GDP. Despite tremendous efficiency measures taken by the health care industry in the last few decades, the net amount of monies spent on health care continues to rise, and the system seems to become less efficient as time progresses. In addition, human beings are living longer but often with chronic stress, related to modern lifestyle, and chronic disease. This stress contributes to the formation of chronic disease and makes management of these diseases less efficient.

When it comes to stress management and wellness, there is a gap between what Americans want from their health care system and what they get, according to various surveys by the American Psychological Association (APA).

Findings from Stress in America™: "Missing the Health Care Connection", which was conducted online by Harris Interactive among 2,020 U.S. adults in August of 2016, suggest that people are not receiving what they need from their health care providers to manage stress and address lifestyle and behavior changes to improve their health.

While Americans think it is important that health care focuses on issues related to stress and living healthier lifestyles, their experiences do not seem to match up with what they value. For example, though 32 percent of Americans say it is very/extremely important to talk with their health care providers about stress management, only 17 percent report that these conversations are happening often or always.

"When people receive professional help to manage stress and make healthy behavior changes, they do better at achieving their health goals," says APA CEO Norman B. Anderson, PhD. "Unfortunately, our country's health system often neglects psychological and behavioral factors that are essential to managing stress and chronic diseases. For our nation to get healthier, lower the rates of chronic illnesses, and lower health care costs, we need to improve how we view and treat stress and unhealthy behaviors that are contributing to the high incidence of disease in the U.S."

Americans who receive little or no stress or behavior management support from their health care provider are especially vulnerable. This is a sizeable group, with slightly more than half (53 percent) of Americans saying they receive little or no support for stress management from their providers, and 39 percent saying that they have little or no behavior management support. The same respondents were more likely to indicate that their stress increased in the past year compared to those who do get support from their health care provider (38 percent with little/no support versus 29 percent with a lot/great deal of support). The situation appears to be worse for the 20 percent of Americans who report experiencing extreme stress (an 8, 9 or 10 on a 10-point scale). More than two-thirds of U.S. adults with high stress (69 percent) say their stress has increased in the past year, yet 33 percent of U.S. adults say that they never discuss ways to manage stress with their health care provider.

Survey findings also show that Americans struggle to keep their stress to levels they believe are healthy. Even though average stress levels across the country appear to be declining (4.9 on a 10-point scale versus 5.2 in 2011), stress levels continue to surpass what Americans define as a healthy level of stress (3.6 on a 10-point scale). And for many Americans, stress is on the rise—35 percent of Americans say their stress increased this past year. "Seventy-five percent of health-care costs are associated with chronic illnesses," experts report, and "what's a key driver of chronic illnesses? Stress."

According to the survey results, while Americans without a chronic health problem had a 5.2 stress rating, people who were depressed had an average stress rating of 6.3, and people who were obese had a 6.0 rating.

"Somehow our health-care system is not focusing on stress," "It's waiting until everybody is sick and then handing out biomedical interventions to help you with your disease, so we're left with more people getting chronic illnesses unnecessarily and increasing health-care costs."

The current state of psychological assessment of stress can be divided into two general areas. The first is traditional psychometric assessments. The system of psychological assessment has not fundamentally changed in many decades. It is based on the idea of the subject of the assessment performing a task and in the most optimal condition an expert examiner scoring the subject. This method has been shown to be fundamentally weak as it can only produce ordinal types of data and is thus very limited in its analytical capabilities.

The second, and more modern type of assessment, is a psychophysiological type of assessment that combines a behave trigger and either a biological measurement or some combination of biological and task measurement. A good example of this type of assessment is a structured brain mapping assessment. These assessments are typically conducted using a 19 channel (channel number can vary) QEEG systems wherein the subject is required to close their eyes and the resulting patterns can be subject to analysis by way of a normative data set. In addition to brain mapping other psychophysiological tests are based on Galvanic Skin response, Heart Rate and Heart Rate Variability and Electromyographic signals and various neuroimaging process including fMRI and PET scans.

Recent scientific studies have demonstrated a relationship between the Activation and Deactivation of the MCO-S to be a highly sensitive measurement of brain network stress. In addition, there are many peer reviewed scientific studies that demonstrate that breath control, interval fitness exercises and direct self-regulation of brain waves can strengthen the Resting State Network and reduce the effects of stress on humans. This later set of Intentional Behavior Modification effects are skills that can be learned. They are more naturally pronounced in some people and can be less developed in others. However, they are subject to being optimized through feedback learning. This feedback learning optimizes biological patterns of intentional oxygen, parasympathetic and brain wave regulation that can fortify humans from stressors as this feedback learning increases the plasticity of the biological system.

In addition, the neurobiological effects of physical exercise are numerous and involve a wide range of interrelated effects on brain structure, brain function, and cognition. A large body of research in humans has demonstrated that consistent aerobic exercise (e.g., 30 minutes every day) induces persistent improvements in certain cognitive functions, healthy alterations in gene expression in the brain, and beneficial forms of neuroplasticity and behavioral plasticity. Some of these long-term effects include: increased neuron growth, increased neurological activity (e.g., c-Fos and BDNFsignaling), improved stress coping, enhanced cognitive control of behavior, improved declarative, spatial, and working memory, and structural and functional improvements in brain structures and pathways associated with cognitive control and memory. The effects of exercise on cognition have important implications for improving academic performance in children and college students, improving adult productivity, preserving cognitive function in old age, preventing or treating certain neurological disorders, and improving overall quality of life.

In healthy adults, aerobic exercise has been shown to induce transient effects on cognition after a single exercise session and persistent effects on cognition following regular exercise over the course of several months. People who regularly perform aerobic exercise (e.g., running, jogging, brisk walking, swimming, and cycling) have greater scores on neuropsychological function and performance tests that measure certain cognitive functions, such as attentional control, inhibitory control, cognitive flexibility, working memory updating and capacity, declarative memory, spatial memory, and information processing speed. The transient effects of exercise on cognition include improvements in most executive functions (e.g., attention, working memory, cognitive flexibility, inhibitory control, problem solving, and decision making) and information processing speed for a period of up to 2 hours after exercising.

Aerobic exercise induces short- and long-term effects on mood and emotional states by promoting positive affect, inhibiting negative affect, and decreasing the biological response to acute psychological stress. Over the short-term, aerobic exercise functions as both an antidepressant and euphoriant whereas consistent exercise produces general improvements in mood and self-esteem.

Regular aerobic exercise improves symptoms associated with a variety of central nervous system disorders and may be used as an adjunct therapy for these disorders. There is clear evidence of exercise treatment efficacy for major depressive disorder and attention deficit hyperactivity disorder. The American Academy of Neurology's clinical practice guideline for mild cognitive impairment indicates that clinicians should recommend regular exercise (two times per week) to individuals who have been diagnosed with this condition. Reviews of clinical evidence also support the use of exercise as an adjunct therapy for certain neurodegenerative disorders, particularly Alzheimer's disease and Parkinson's disease. Regular exercise is also associated with a lower risk of developing neurodegenerative disorders. A large body of preclinical evidence and emerging clinical evidence supports the use of exercise therapy for treating and preventing the development of drug addictions. Regular exercise has also been proposed as an adjunct therapy for brain cancers.

Neuroplasticity

Neuroplasticity is the process by which neurons adapt to a disturbance over time, and most often occurs in response to repeated exposure to stimuli. Aerobic exercise increases the production of neurotrophic factors (e.g., BDNF, IGF-1, VEGF) which mediate improvements in cognitive functions and various forms of memory by promoting blood vessel formation in the brain, adult neurogenesis, and other forms of neuroplasticity. Consistent aerobic exercise over a period of several months induces clinically significant improvements in executive functions and increased gray matter volume in nearly all regions of the brain, with the most marked increases occurring in brain regions that give rise to executive functions. The brain structures that show the greatest improvements in gray matter volume in response to aerobic exercise are the prefrontal cortex, caudate nucleus, and hippocampus; less significant increases in gray matter volume occur in the anterior cingulate cortex, parietal cortex, cerebellum, and nucleus accumbens. The prefrontal cortex, caudate nucleus, and anterior cingulate cortex are among the most significant brain structures in the dopamine and norepinephrine systems that give rise to cognitive control. Exercise-induced neurogenesis (i.e., the increases in gray matter volume) in the hippocampus is associated with measurable improvements in spatial memory. Higher physical fitness scores, as measured by $VO_2$ max, are associated with better executive function, faster information processing speed, and greater gray matter volume of the hippocampus, caudate nucleus, and nucleus accumbens. Long-term aerobic exercise is also associated with persistent beneficial epigenetic changes that result in improved stress coping, improved cognitive function, and increased neuronal activity (c-Fos and BDNF signaling).

Structural Growth

Reviews of neuroimaging studies indicate that consistent aerobic exercise increases gray matter volume in nearly all regions of the brain, with more pronounced increases occurring in brain regions associated with memory processing, cognitive control, motor function, and reward. The most prominent gains in gray matter volume are seen in the prefrontal cortex, caudate nucleus, and hippocampus, which support cognitive control and memory processing, among other cognitive functions. Moreover, the left and right halves of the prefrontal cortex, the hippocampus, and the cingulate cortex appear to become more functionally interconnected in response to consistent aerobic exercise. Three reviews indicate that marked improvements in prefrontal and hippocampal gray matter volume occur in healthy adults that regularly engage in medium intensity exercise for several months. Other regions of the brain that demonstrate moderate or less significant gains in gray matter volume during neuroimaging include the anterior cingulate cortex, parietal cortex, cerebellum, and nucleus accumbens.

Regular exercise has been shown to counter the shrinking of the hippocampus and memory impairment that naturally occurs in late adulthood. Sedentary adults over age 55 show a 1-2% decline in hippocampal volume annually. A neuroimaging study with a sample of 120 adults revealed that participating in regular aerobic exercise increased the volume of the left hippocampus by 2.12% and the right hippocampus by 1.97% over a one-year period. Subjects in the low intensity stretching group who had higher fitness levels at baseline showed less hippocampal volume loss, providing evidence for exercise being protective against age-related cognitive decline. In general, individuals that exercise more over a given period have greater hippocampal volumes and better memory function. Aerobic exercise has also been shown to induce growth in the white matter tracts in the anterior corpus callosum, which normally shrink with age.

The various functions of the brain structures that show exercise-induced increases in gray matter volume include:

Prefrontal and anterior cingulate cortices—required for the cognitive control of behavior, particularly: working memory, attentional control, decision-making, cognitive flexibility, social cognition, and inhibitory control of behavior, implicated in attention deficit hyperactivity disorder (ADHD) and addiction.

Nucleus accumbens—responsible for incentive salience ("wanting" or desire, the form of motivation associated with reward) and positive reinforcement; implicated in addiction.

Hippocampus—responsible for storage and consolidation of declarative memory and spatial memory, implicated in depression.

Cerebellum—responsible for motor coordination and motor learning.

Caudate nucleus—responsible for stimulus-response learning and inhibitory control, implicated in Parkinson's disease, Huntington's disease and ADHD.

Parietal cortex—responsible for sensory perception, working memory, and attention.

Long-Term Effects on Cognition

Concordant with the functional roles of the brain structures that exhibit increased gray matter volumes, regular exercise over a period of several months has been shown to persistently improve numerous executive functions and several forms of memory. In particular, consistent aerobic exercise has been shown to improve attentional control, information processing speed, cognitive flexibility (e.g., task switching), inhibitory control, working memory updating and capacity, declarative memory, and spatial memory. In healthy young and middle-aged adults, the effect sizes of improvements in cognitive function are largest for indices of executive functions and small to moderate for aspects of memory and information processing speed. It may be that in older adults, individuals benefit cognitively by taking part in both aerobic and resistance type exercise of at least moderate intensity. Individuals who have a sedentary lifestyle tend to have impaired executive functions relative to other more physically active non-exercisers. A reciprocal relationship between exercise and executive functions has also been noted: improvements in executive control processes, such as attentional control and inhibitory control, increase an individual's tendency to exercise.

Psychological Stress

The "stress hormone", cortisol, is a glucocorticoid that binds to glucocorticoid receptors Psychological stress induces the release of cortisol from the adrenal gland by activating the hypothalamic—pituitary—adrenal axis (HPA axis). Short-term increases in cortisol levels are associated with adaptive cognitive improvements, such as enhanced inhibitory control. However, excessively high exposure or prolonged exposure to high levels of cortisol causes impairments in cognitive control and has neurotoxic effects in the human brain. For example, chronic psychological stress decreases BDNF expression which has detrimental effects on hippocampal volume and can lead to depression.

As a physical stressor, aerobic exercise stimulates cortisol secretion in an intensity-dependent manner; however, it does not result in long-term increases in cortisol production since this exercise-induced effect on cortisol is a response to transient negative energy balance individuals who have recently exercised exhibit improvements in stress coping behaviors. Aerobic exercise increases physical fitness and lowers neuroendocrine (i.e., HPA axis) reactivity and therefore reduces the biological response to psychological stress in humans (e.g., reduced cortisol release and attenuated heart rate response). Exercise also reverses stress-induced decreases in BDNF expression and signaling in the brain, thereby acting as a buffer against stress-related diseases like depression.

Continuous exercise can produce short-term euphoria, an affective state associated with feelings of profound contentment, elation, and well-being, which is colloquially known as a "runner's high" in distance running or a "rower's high" in rowing. Current medical reviews indicate that several endogenous euphoriants are responsible for producing exercise-related euphoria, specifically phenethylamine (an endogenous psychostimulant), β-endorphin (an endogenous opioid), and anandamide (an endocannabinoid).

Sibley and Etnier (2003) performed a meta-analysis that looked at the relationship between physical activity and cognitive performance in children. They reported a beneficial relationship in the categories of perceptual skills, intelligence quotient, achievement, verbal tests, mathematic tests, developmental level/academic readiness and other, with the exception of memory, that was found to be unrelated to physical activity. The correlation was strongest for the age ranges of 4-7 and 11-13 years. On the other hand, Chaddock and colleagues (2011) found results that contrasted Sibley and Etnier's meta-analysis. In their study, the hypothesis was that lower-fit children would perform poorly in executive control of memory and have smaller hippocampal volumes compared to higher-fit children. Instead of physical activity being unrelated to memory in children between 4 and 18 years of age, it may be that preadolescents of higher fitness have larger hippocampal volumes, than preadolescents of lower fitness. According to a previous study done by Chaddock and colleagues (Chaddock et al. 2010), a larger hippocampal volume would result in better executive control of memory. They concluded that hippocampal volume was positively associated with performance on relational memory tasks. Their findings are the first to indicate that aerobic fitness may relate to the structure and function of the preadolescent human brain. In Best's (2010) meta-analysis of the effect of activity on children's executive function, there are two distinct experimental designs used to assess aerobic exercise on cognition. The first is chronic exercise, in which children are randomly assigned to a schedule of aerobic exercise over several weeks and later assessed at the end. The second is acute exercise, which examines the immediate changes in cognitive functioning after each session the results of both suggest that aerobic exercise may briefly aid children's executive function and also influence more lasting improvements to executive function. Other studies have suggested that exercise is unrelated to academic performance, perhaps due to the parameters used to determine exactly what academic achievement is. This area of study has been a focus for education boards that make decisions on whether physical education should be implemented in the school curriculum, how much time should be dedicated to physical education, and its impact on other academic subjects.

Another study found that sixth-graders who participated in vigorous physical activity at least three times a week had the highest scores compared to those who participated in moderate or no physical activity at all. The kids who participated in vigorous physical activity scored three points higher, on average, on their academic test, which consisted of math, science, English, and world studies.

Animal studies have also shown that exercise can impact brain development early on in life. Mice that had access to running wheels and other such exercise equipment had better neuronal growth in the neural systems involved in learning and memory. Neuroimaging of the human brain has yielded similar results, where exercise leads to changes in brain structure and function. Some investigations have linked low levels of aerobic fitness in children with impaired executive function in older adults, but there is mounting evidence it may also be associated with a lack of selective attention, response inhibition, and interference control.

Clinical and preclinical evidence indicate that consistent aerobic exercise, especially endurance exercise (e.g., marathon running), actually prevents the development of certain drug addictions and is an effective adjunct treatment for drug addiction, and psychostimulant addiction in particular. Consistent aerobic exercise magnitude-dependently (i.e., by duration and intensity) reduces drug addiction risk, which appears to occur through the reversal of drug-induced, addiction-related neuroplasticity. One review noted that exercise may prevent the development of drug addiction by altering ΔFosB or c-Fos immunoreactivity in the striatum or other parts of the reward system. Moreover, aerobic exercise decreases psychostimulant self-administration, reduces the reinstatement (i.e., relapse) of drug-seeking, and induces opposite effects on striatal dopamine receptor $D_2$ (DRD2) signaling (increased DRD2 density) to those induced by pathological stimulant use (decreased DRD2 density). Consequently, consistent aerobic exercise may lead to better treatment outcomes when used as an adjunct treatment for drug addiction. As of 2016, more clinical research is still needed to understand the mechanisms and confirm the efficacy of exercise in drug addiction treatment and prevention.

While the science is still developing, it is clear that managing stress and physical activity have important implications not just for conventional measures of physical health, but also for overall well-being and mental performance. In addition, the Default Mode Network appears to have the potential to play an important role in managing stress, optimizing cognitive function, optimizing health and fitness and many other factors related to wellness. Unfortunately, relatively little progress has been made towards harnessing the ability of individuals to optimize the Default Mode Network to achieve such objectives.

SUMMARY OF THE INVENTION

The present invention is directed to assessing a subject's Default Mode Network through corresponding measurements of the Micro-Coherence Oximetry Network Strength (MCO-S). In addition, the present invention addresses optimization of MCO-S in relation to desired objectives through deep behavior modification. These techniques can be applied to address a variety of objectives such as improving cognition, reducing brain fog, managing stress, and optimizing health and fitness.

The current invention addresses issues noted above by strengthening the MCO Network through an AI driven Deep Behavior Modification process. Deep Behavior Modification is the integration of artificial intelligence (machine learning) directed self-regulation programs in breath control, interval fitness and direct brain wave regulation, combined with cognitive and behavioral restructuring programs on the user's smart phone, all intended for stress management, brain fog reduction and executive function optimization, and to enhance peer to peer MCO Network communication.

The current invention integrates a plasticity measurement into the MCO-S assessment. This plasticity measurement is aimed at measuring the degree of voluntary biological fortification capacity a human has to aid in the management of stress especially under conditions where environmental stressors are having a significantly negative effect on the MCO-S. The invention further, through its AI programming function, lays out a plasticity optimization program (intentional behavior modification program) to optimize this plasticity for stress management.

In accordance with one aspect of the present invention, a utility (encompassing a system, component devices and associated methodology) is provided for assessing and optimizing a Default Mode Network of a subject. The system involves providing a sensor device including one or more sensors for sensing signals indicative of at least one of subject brain waves, heart rate variability and galvanic skin conductance. For example, the sensor device may include pulse oximetry instrumentation and/or EEG sensors. The sensor device can then be applied to a subject to obtain measurements of signals when the subject is in a selected state that has a known correlation to a Default Mode Network of a nervous system. In one implementation, measurements are obtained with the subject's eyes closed corresponding to Default Mode Network activation and measurements are also taken with the patient's eyes open corresponding to Default Mode Network deactivation. The measurements can then be used for at least one of assessment of the Default Mode Network and optimization of the Default Mode Network in relation to a defined objective.

As noted above, the sensor device may include pulse oximetry instrumentation and/or EEG sensors. The pulse oximetry instrumentation can be used to obtain arterial oxygen saturation information as well as heart rate information. This information can be further processed to obtain additional information such as heart rate variability. The EEG sensors may be used to obtain information regarding one of a brainwave theta-beta ratio, an alpha wave and alpha wave coherence.

Measurements from the sensor device may be used for assessment of the Default Mode Network or for optimization in relation to a defined objective. Assessment may involve determining a strength value related to the Default Mode Network and one or more variability values. Such assessment may involve taking measurements under a number of conditions. As noted above, measurements may be taken with the subject's eyes open and with the subject's eyes closed. In addition, measurements may be taken in connection with one or more intentional variability training exercises performed by the subject. These may include, for example, an activity to induce a blood oxygen desaturation event, a deep breathing exercise, a state of mental concentration, a state of problem-solving, and a state of active pattern recognition. The subject may also provide a voice tract. The results of these measurements under various conditions can be combined to yield an overall strength value related to the Default Mode Network. In addition, variability results may be indicated by individual measurements or various combinations thereof.

Information from such an assessment may be used to develop an optimization protocol for optimizing the Default Mode Network in relation to a defined objective. The optimization protocol may be developed by employing a processing system to determine at least a selected set of Default Mode Network exercises and a set of parameters for executing the exercises. The processing system may implement machine learning to progressively optimize the Default Mode Network in relation to the defined objective. For example, the optimization protocol may be developed to optimize an objective related to one of fitness and athletic performance, reducing mental fog or increasing concentration, or managing stress levels. The system may include the noted sensor device (which may, for example, be embodied in a headband), a user device (such as a cell phone or other mobile device and/or a VR headset) and a processing platform that may be local or cloud-based. Each of these elements has novel features and functionality in relation to the context described above.

BRIEF DESCRIPTION OF THE DRAWINGS

For a more complete understanding of the present invention and further advantages thereof, reference is now made to the following detailed description, taken in conjunction with the drawings, in which.

DETAILED DESCRIPTION

In the following description, the invention is set forth in the context of a system including a headband for obtaining pulse oximetry and EEG measurements, smart phone based applications for MCO-S assessment and deep behavior modification, and a cloud-based processing platform for executing artificial intelligence to support the noted applications. While this is believed to be particularly advantageous implementation of the present invention, it will be appreciated that different sensors, different variables and different logic distributed over different machines are possible in accordance with the present invention. Accordingly, the following description should be understood as exemplary and not by way of limitation.

In the following description, the overall system and high level functionality is first described in connection with FIGS. 1-7. Thereafter, further details and specific applications are described.

Figure 1:
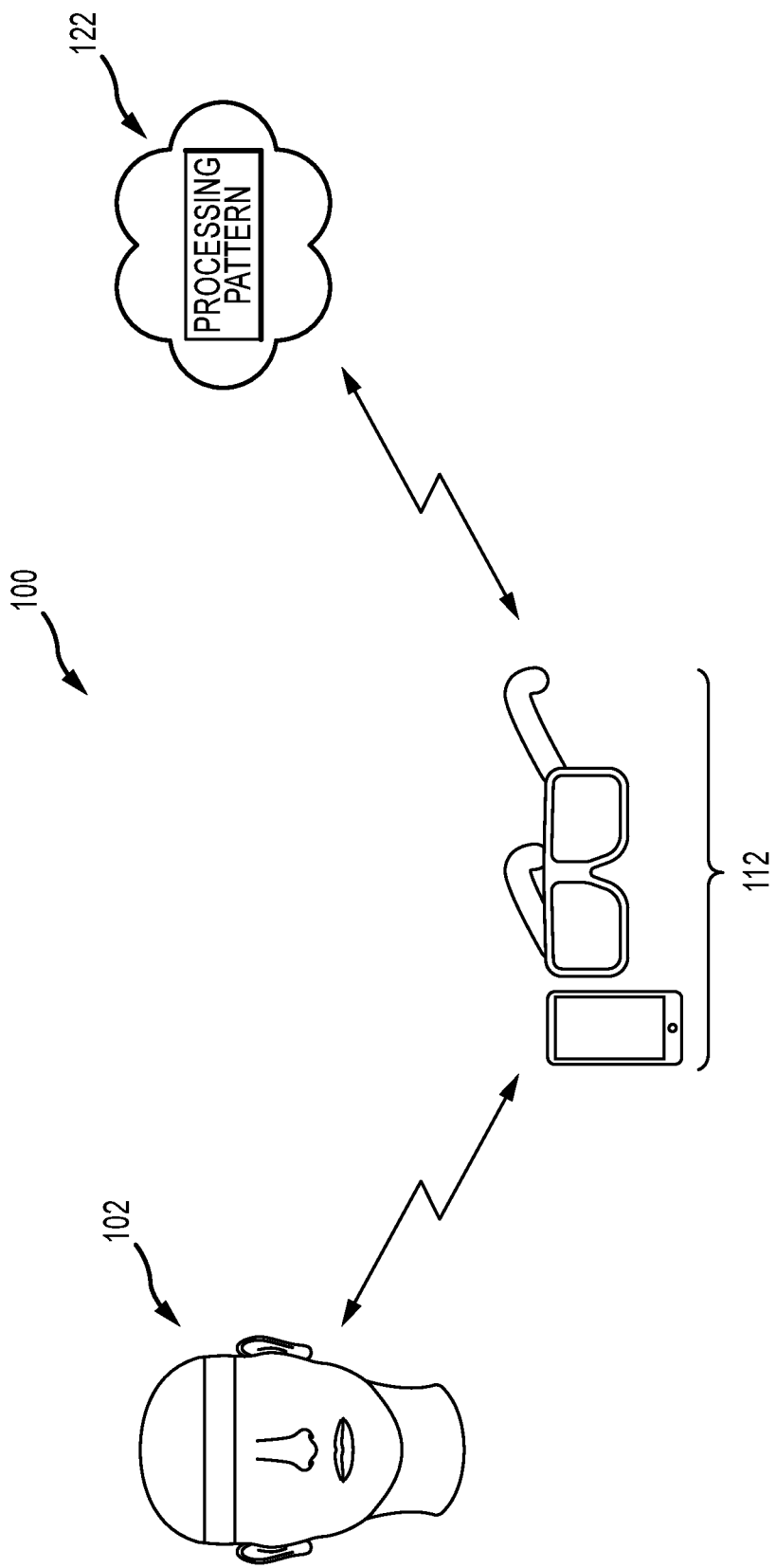
FIG. 1 is a schematic diagram of a MCO-S system in accordance with the present invention.

FIG. 1 illustrates an MCO-S system in accordance with the present invention. Generally, the system 100 includes a wearable 102, a user device 112 and a processing platform 123. Each of these components will be described in more detail below.

The wearable 102 collects subject information sufficient to enable monitoring and optimization of the subject's Default Mode Network or Resting State Network. It will be appreciated that various types of sensors can be used to provide subject information in this regard. As will be described in more detail below, a preferred wearable in accordance with the present invention includes pulse oximetry instrumentation and EEG electrodes to obtain brainwave data, oxygen saturation data, heart rate variability data, galvanic skin conductance data, and/or other data.

In the illustrated embodiment, such sensors are incorporated in a headband such that the sensors maintain appropriate optical, electrical or physical contact with the subject's forehead. For example, the sensors may be mounted on an inside surface of a flexible headband so that the sensor surfaces are in contact with or proximate to the subject's forehead. It will be appreciated, however, that the sensors may be positioned at other locations on the subject's body and that different sensors may optionally be positioned at different locations on separate wearables. For example, pulse oximetry sensors may be disposed on a wristband and EEG sensors may be disposed on the subject's temples or scalp. Furthermore, rather than being incorporated into a headband, the sensors may be incorporated into a VR headset, eyewear, a cap or hat, or other physical embodiment.

As will be described in detail below, information from the sensors may be communicated to a user device 112, such as a cell phone, VR headset, tablet or laptop computer, or other device. As will be described below, the user device 112 may process the sensor data, communicate with a remote platform, lead the subject through assessment and behavior modification protocols, and perform other functions. It will thus be appreciated that certain functionality described herein may be implemented as one or more applications running on a processor of the user device 112.

In the illustrated embodiment, the user device 112 communicates with a remote processing platform 123 that may be cloud-based 122. The processing platform may execute artificial intelligence functionality and other logic in connection with assessing the patient's micro coherence network strength and optimizing behavior modification protocols in relation to attributes and objectives of the subject. Such functionality may be implemented as one or more applications running on one or more processors (e.g., servers) of the processing platform 123. It will be appreciated that the processing platform 123 may be embodied in a single processing machine or in multiple processing machines at a single location or geographically distributed. Moreover, much of the functionality described below may be distributed as desired as between the processing platform 123 and the user device 112. Such distribution may depend on a number of factors such as convenience, processing speed, bandwidth constraints, processing constraints, and the desirability of executing certain functionality off-line.

Figure 2:
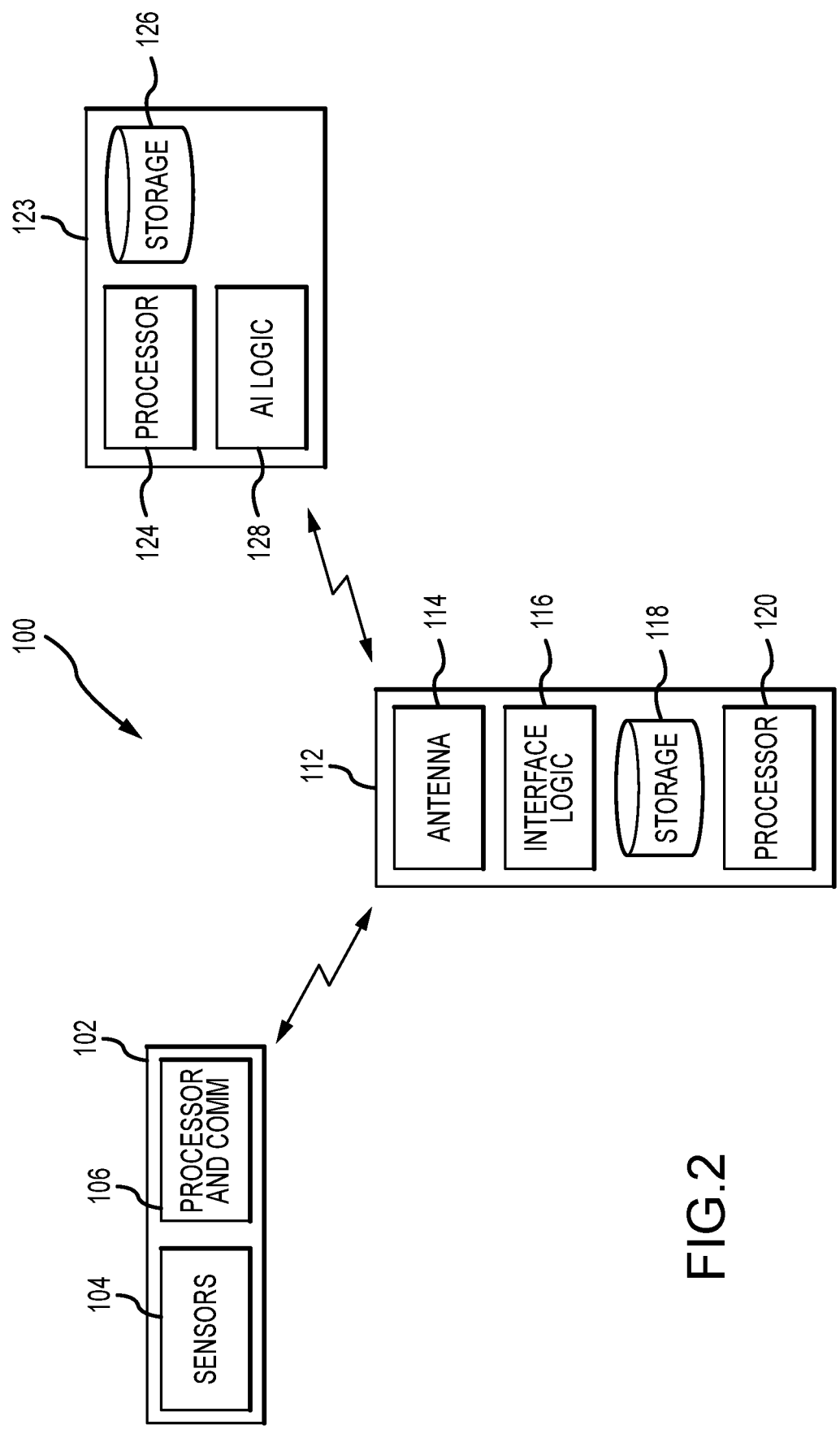
FIG. 2 is a further schematic diagram of the system of FIG. 1.

FIG. 2 shows a high-level schematic of the system 100. As shown, the wearable 102 includes sensors 104 and processor and communication logic 106. The logic 106 may perform a number of functions. In this regard, the logic 106 may acquire subject information from the sensors 104 for transmission to the user device 112. Optionally, the logic 106 may perform a number of pre-processing functions on the data such as analog-to-digital conversion, signal encoding, data compression, formatting and the like. The logic 106 is also operative for a number of functions associated with wireless communication of the data from the wearable 102 to the user device 112. In this regard, the logic 106 may format the data into appropriate messages in accordance with an API or other messaging scheme and may cause the messages to be transmitted via an RF antenna. Optionally, the subject data may be preprocessed to provide processed data rather than raw data.

The illustrated user device 112 includes an antenna 114, a processor 116, storage 118, and interface logic 120. The antenna 114 is operative for communicating with the wearable 102 and with the processing platform 123. Such communications may be conducted via different frequency bands and formats. For example, a short-range wireless communications protocol such as Bluetooth™ may be implemented for communications between the wearable 102 and the user device 112. Communications between the user device 114 and the processing platform 123 may involve a variety of protocols such as wireless network data protocols, IP communications and/or proprietary protocols.

The processor 116 may perform a number of functions in accordance with the present invention. For example, the processor may control acquisition of subject information from the wearable 102, transmit subject information to the processing platform 123, receive processed information from the processing platform 123, control a display of the user device 112 to implement various user interfaces in accordance with the present invention, and execute protocols for assessment and behavior modification. It will be appreciated that the processor 116 may be implemented on a single or multiple processing cores.

The illustrated user device 112 also includes storage for storing various information for use by the system 100. In this regard, the storage may store subject information, generalized or average information related to the Default Mode Network, protocols for intentional variability training, assessment, and behavior modification, and formulas for calculating various factors used by the system 100. The storage 118 may be implemented as onboard storage, removable storage or separate storage accessible by the user device 112.

The illustrated user device 112 further includes interface logic 120. The interface logic 120 is operative to render user interfaces for allowing the user (who may be a subject, a physician or therapist, a researcher or other user) to interact with the system 100. Such interfaces may include graphical user interfaces, sound and tactile outputs, VR displays and the like. The interfaces may prompt the user to execute desired protocols, to input information, provide biofeedback images and the like.

The illustrated processing platform 123 generally includes a processor 124, storage 126 and AI logic 128. Among the functions that are performed by the platform 123 are assessment of MCO-S strength and plasticity, development of optimization protocols, monitoring changes in subject attributes and objectives, and adapting as required. To these ends, the AI logic 128 may continually monitor inputs and develop behavior modification protocols. The processor 124 operates the AI logic 128 and accesses information from storage 126 as needed. As described below, the storage 126 may include subject information, tables, and generalized or average information relevant to various calculations.

Figure 3:
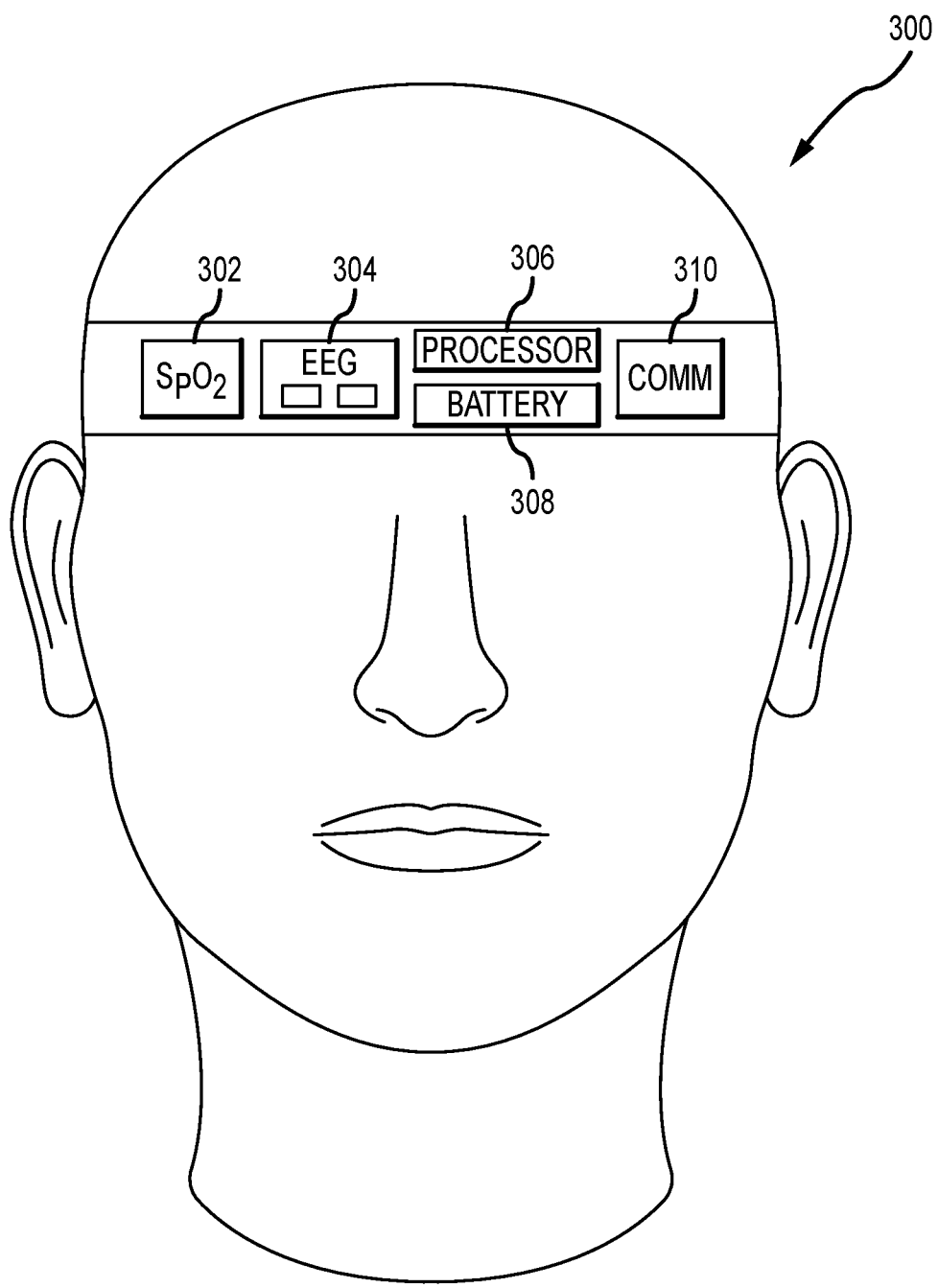
FIG. 3 is a schematic diagram of a wearable in accordance with the present invention.

FIG. 3 shows a more detailed schematic of a wearable 300, in this case, embodied in a headband. The illustrated wearable 300 includes pulse oximetry sensors 302, EEG sensors 304, a processor 306, one or more batteries 308 and communications components 310. The pulse oximetry sensors 302 may include one or more optical sources and one or more optical detectors. For example, the sensors 302 may include LEDs of different wavelengths such as red and infrared. The sensors may further include optical detectors for detecting light from the sources that is reflected from the subject's skin after interacting with arterial blood. The output from the oximetry sensors 302 may be multiple plethysmographs corresponding to multiple wavelengths. These can be processed (e.g., in the wearable, in the user device, and/or at a remote processing platform) to yield information concerning oxygen saturation of the arterial blood, pulse rate, variability of pulse rate, and other information.

The EEG sensors 304 may include multiple electrodes for detecting and monitoring brain activity. The output from the sensors 304 may comprise multiple brainwave readouts. This information may be processed to obtain information concerning theta-beta ratios, alpha-theta ratios, alpha wave waveforms and the like. As described below, these waveforms can be analyzed to monitor various parameters related to MCO-S.

The processor 306 can be used to operate the sensors 302 and 304, process the outputs from the sensors 302 and 304, and control communications between the wearable 300 and a user device. The battery 308 provides power for the other components. Preferably, the battery 308 is rechargeable. The illustrated wearable 300 also includes a communications module 310 for managing communications with a user device. In this regard, the module 310 may operate an RF antenna and provide various functions related to formatting, multiplexing, and the like.

Figure 4:
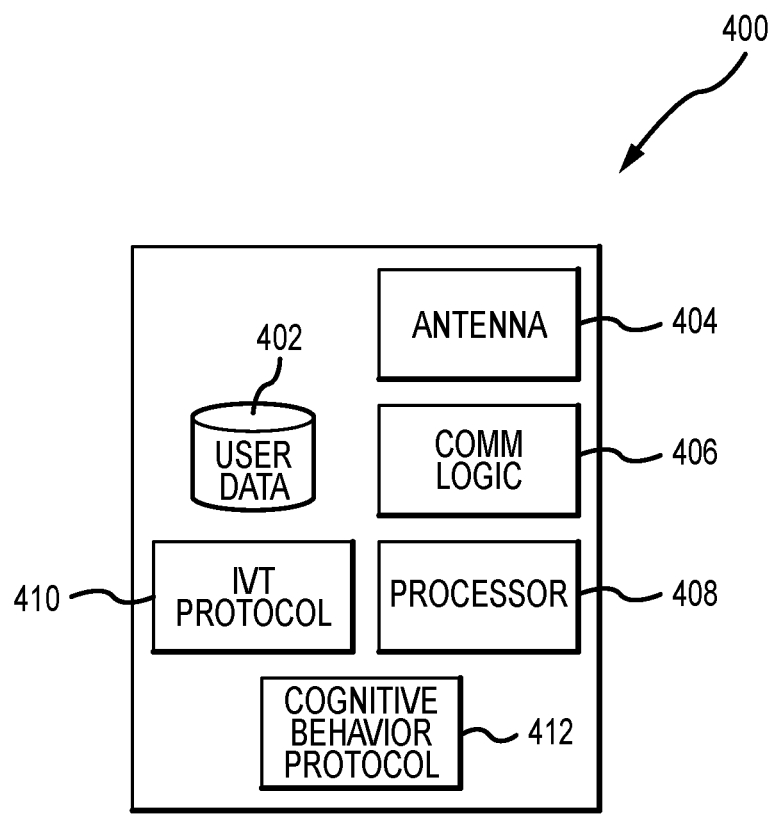
FIG. 4 is a schematic diagram of a user device in accordance with the present invention.

FIG. 4 shows a more detailed schematic of the user device 400. In the illustrated embodiment, the user device 400 includes an antenna 404 for communicating wirelessly with the wearable and with the remote processing platform. As discussed above, this may include communications via different wavelength bands and protocols. The device 400 further includes storage 402 for storing information for use by the MCO-S system. This may include subject information, user information, protocol information, preferences, settings, objectives and other information.

The communications logic 406 can operate the antenna 404 to communicate with the wearable and with the processing platform. Such communications may be triggered by user inputs, triggered by events such as incoming sensor data, or performed automatically or periodically. The IVT protocol 410 includes logic to implement the various intentional variability training measurements as described below. Similarly, the cognitive behavior protocol 412 includes logic for implementing behavior modification exercises as described herein. The processor 408 accesses the data from storage 402 and executes the various logical components.

Figure 5:
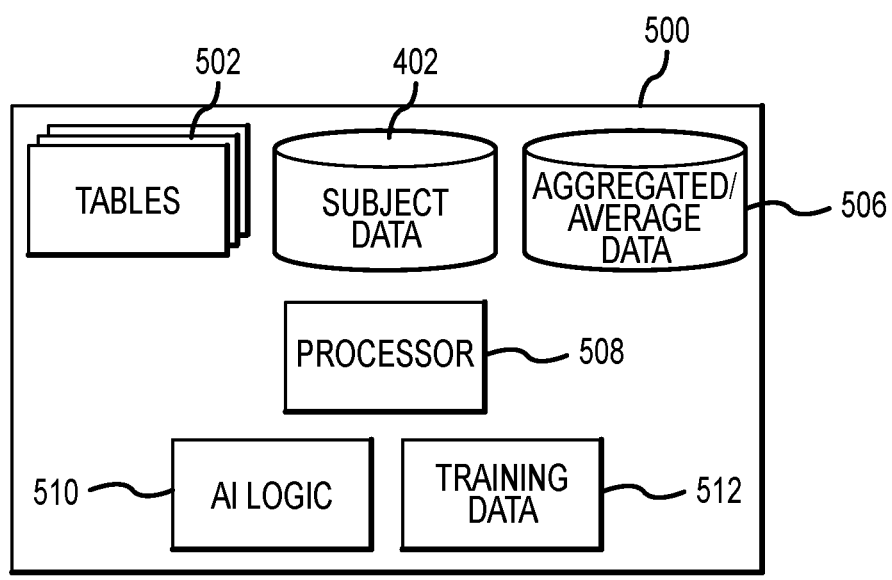
FIG. 5 is a schematic diagram of a processing platform in accordance with the present invention.

FIG. 5 shows a more detailed schematic of the processing platform 500. As discussed above, the processing platform may be cloud-based and may be implemented in a single machine or in multiple machines at one location or geographically distributed. The illustrated platform 500 includes a number of tables 502 as described herein which may include a descriptive data table and a performance data table. The illustrated platform further includes storage components 504 and 506 for storing subject data and aggregated or average data. It will be appreciated that, in many cases, the subject data will need to be interpreted in relation to average or aggregated data for a larger population.

The AI logic 510 is used to assess and optimize MCO-S in relation to subject attributes and objectives. For example, the AI logic 510 may determine an optimal set of IVT exercises as well as optimal settings for those exercises for a particular subject based on the objectives of the subject (e.g., reduce brain fog or optimize athletic training) in relation to patient attributes (e.g., which permutations of the IVT exercises take advantage of the greatest elasticity of MCO-S). The AI logic 510 may use training data 512 as well as subject data monitored on an ongoing basis to tune the performance of the AI logic to achieve the subject's objectives. The processor 508 can access the storage 504 and 506 as well as the tables 502 and execute the AI logic 510.

Figure 6:
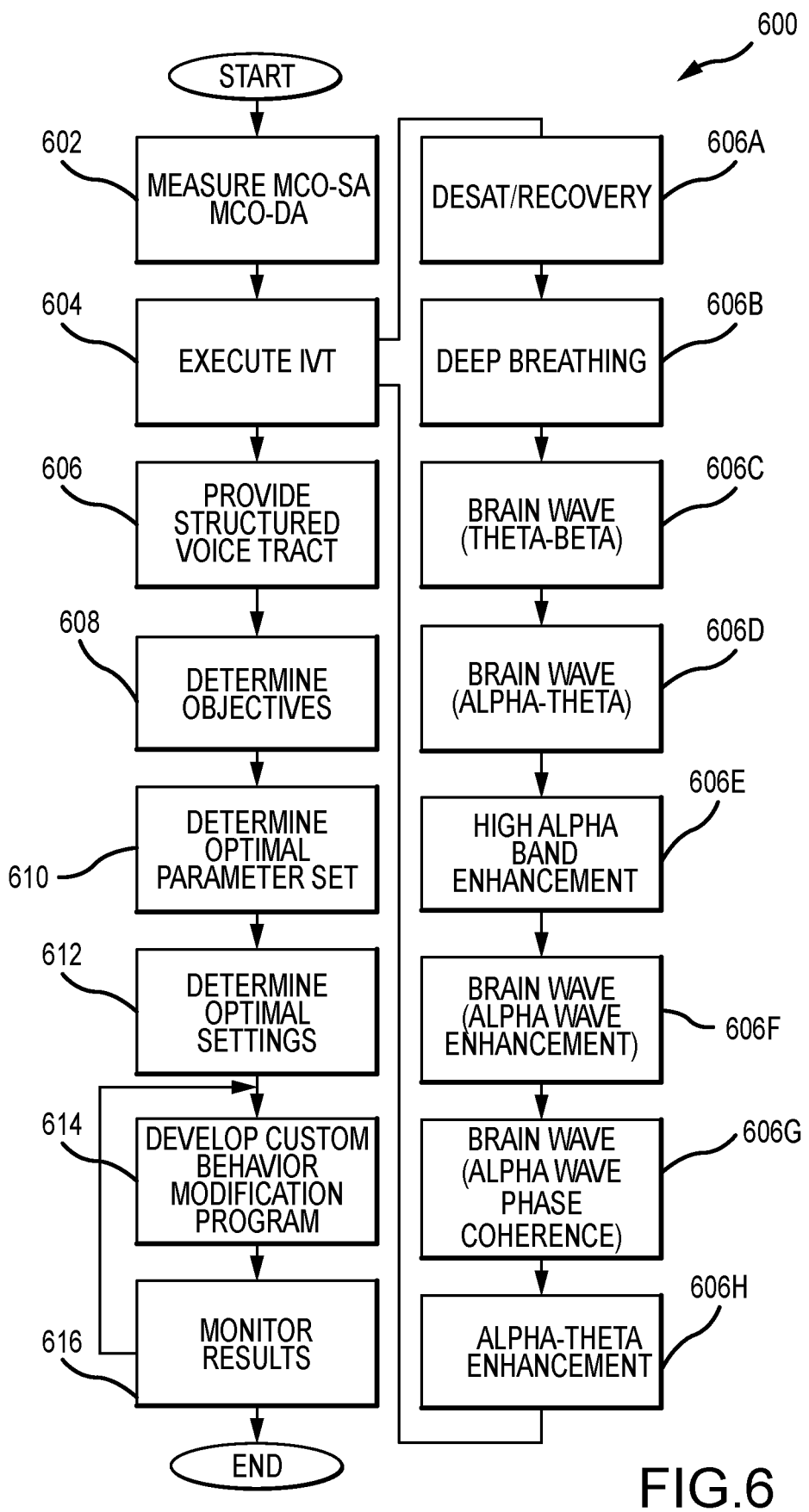
FIG. 6 is a flowchart of an MCO-S assessment and optimization process in accordance with the present invention.

FIG. 6 illustrates an MCO-S assessment and optimization process 600 in accordance with the present invention. The process 600 is initiated by measuring (602) MCO activation and MCO deactivation. For example, this may be done by taking measurements with the subject's eyes closed so as to activate the Default Mode Network and taking measurements with the subject's eyes open. The intentional variability training exercises can then be executed (604). As described in more detail below, these may include a desaturation and recovery exercise 606A, a deep breathing exercise 606B, a theta-beta brainwave exercise 606C, and alpha-theta brainwave exercise 606D, high alpha band enhancement exercise 606E, alpha wave enhancement exercise 606F, and an alpha wave phase coherence exercise 606G and an alpha-theta enhancement exercise 606H. The subject may also be prompted to provide (606) a structured voice track. All of the foregoing can be used to determine nominal or baseline MCO-S values.

The process 600 continues with determining (608) objectives of the subject. As described below, a number of objectives can be addressed by the system of the present invention including, for example, reducing brain fog, increasing concentration, improving overall health, optimizing athletic training, reducing stress, and otherwise enhancing wellness. Artificial intelligence can then be applied to determine (610) an optimal parameter set and to determine (612) optimal settings. For example, the system may determine an optimal set of the IVT exercises as well as times, durations, and frequencies for the various exercises to optimize the benefit to the subject in relation to the subject's objectives. Based on biofeedback and other information, the system can develop (614) and evolve a custom behavior modification program including the IVT exercises and other actions by the subject to achieve the desired objectives. The system can monitor (616) the results of the behavior modification program and adapt the behavior modification program as necessary.

Figure 7:
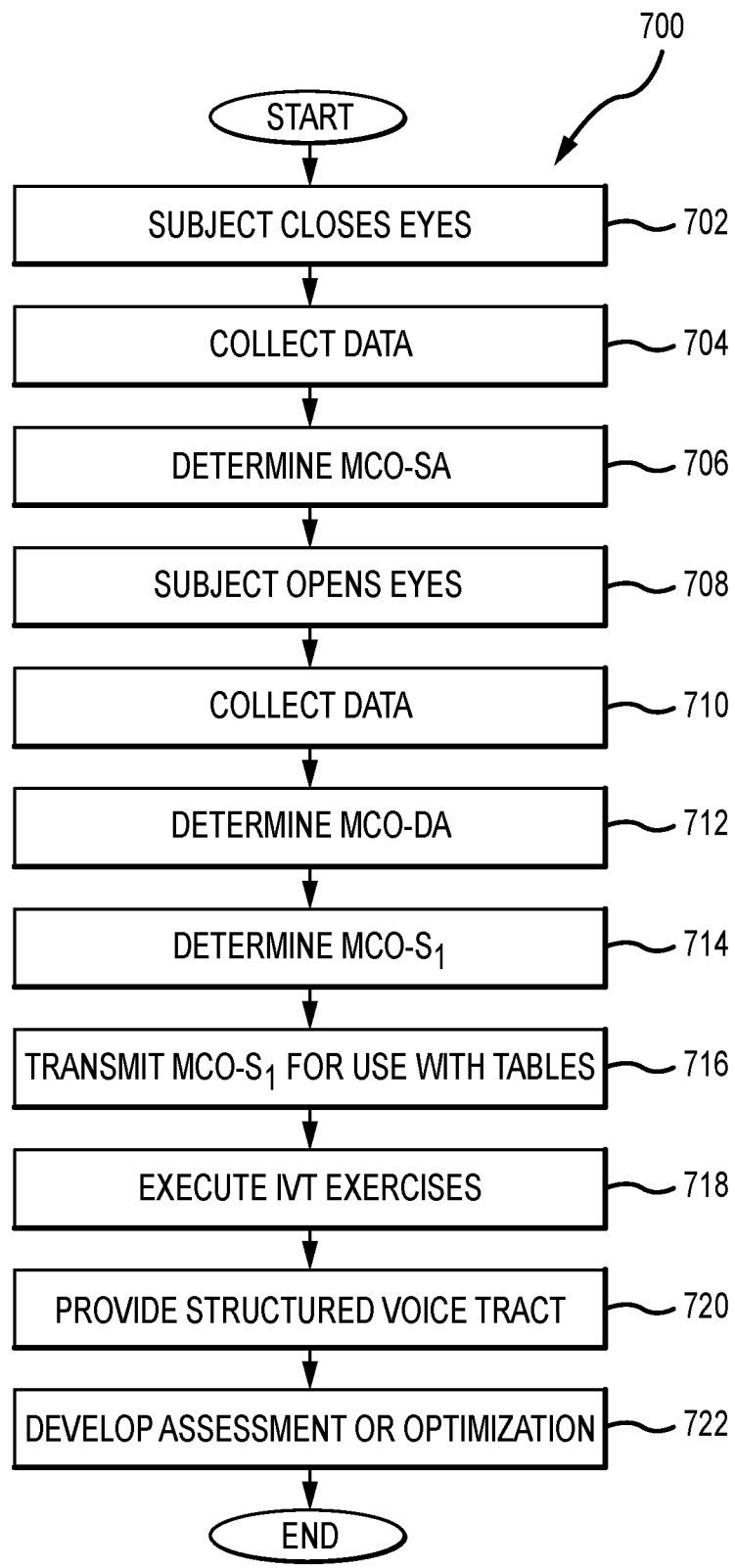
FIG. 7 is a further flowchart of an MCO-S assessment and optimization process in accordance with the present invention.

FIG. 7 shows a more detailed process 704 for MCO-S assessment and optimization. The process 700 begins with asking the subject to close (702) his eyes. Data can then be collected (704) from all sensors and used to determine (706) an MCO activation measurement. The subject can then be instructed to open (708) his eyes. Data can again be collected (710) from all sensors and used to determine (712) an MCO deactivation measurement. An initial value of MCO-S can then be determined (714) as a difference between the activation and deactivation measurements.

This initial value can then be transmitted (716) to the processing platform for use with the tables for purposes of assessment and/or optimization. The subject can then execute (718) the various IVT exercises as described herein. Measurements may be taken from all sensors in connection with the exercises. In addition, the subject may be instructed to provide (720) a structured voice track. All of the above information, including MCO-S, the data from the IVT exercises and the structured voice track, may be used to develop (722) an assessment or optimization protocol related to the Default Mode Network.

Having thus described the overall system and high level functionality, further details and specific applications will now be described. In particular, the following sections, describe functionality for assessing MCO-S strength, processors for deep behavior modification, and process for a specific optimization application related to health and fitness.

MCO-S Assessment

The Micro-Coherence Oximetry Network Strength MCO-S application is aimed at assessing the strength of the human Micro-Coherence Oximetry Network Strength (MCO-S). The measurement is initiated by the collection of various bio sensors on the human forehead that measure brain waves, pulse oximetry, heart rate variability and galvanic skin conductance data.

This application performs this measurement by way of measuring the Micro-Coherence Oximetry Network Strength Activation and Deactivation differences with or without combining this measurement with a biological Intentional Variability Training (IVT) measurement, scaling the measurement for total a strength measurement and then translating this assessment into a numeric scale or Virtual Realty immersive experience.

The MCO-S Network is a measurement that is a corresponding measurement to the human nervous system Default Mode Network. The Default Mode Network is a reflex network that is triggers when a person closes their eyes and "rests" It is also known as the Resting State Network. It is an overall nervous system network that has been measured using brain EEG measurements, neuroimaging measurements including fMRI, PET and magnetoencephalography. It has also been measured using Heart Rate Variability and Galvanic Skin conductance. It can be trigger as a reflex by all human beings and as it is a reflex and does not require a mindful effort or training and is independent of the subject's knowledge level. It is therefore cross-cultural, independent of education and of IQ.

The MCO-S measurement is compared to a set of two types of data tables. These are descriptive data tables and performance data tables each containing unstructured commercial data and structured scientific study data Each table has an initiating data cell for age related averages of the activation and deactivation with or without intentional variability data. The descriptive data tables provide for various descriptive categories. The performance data tables provide for, intentional variability data, cognitive restructuring data and voice pattern analysis data.

The Intentional Variability metric is based on a set of intentional behavior modification exercise measurements in breath control, precision exercise intervals, and self-regulated brain wave exercises. The system calculates a table of permutation change patterns related to the intentional variability exercises and ranks them with respect to age and descriptive characteristic.

The cognitive behavior training metric is derived from various cognitive behavior training data often collected on the subject's smart phone or VR device.

The invention is composed of a forehead bio sensor headband composed of brain wave sensors, pulse oximetry, HRV and galvanic skin response conductance (MCO Headband). The MCO headband wirelessly transmits a data stream to the user's smart phone or is integrated with a VR device.

MCO-S is determined by a set of structured assessments. These assessments are assessments completed in a Practitioners office, Assessment completed by an individual at home and an Integration of data from the first two Assessments.

Assessment Data is transmitted from the device. The assessment subject is instructed to close the subject eyes and data is collected on all sensor transmissions. This is called MCO-S Activation or MCO-SA. The subject is then instructed to open the subject eyes this is called Deactivation or MCO-DA. A difference measurement is made on all sensor data by way of subjecting the MCO-SA-MCO-DA. The greater the difference is correlated with MCO-S. This represent a level one measurement and the Level I measurement is transmitted to the two data tables.

The subject is instructed in 5 intentional variability activities.

The subject is instructed in a desaturation exercise by way of a stationary bike or plank test or other physical demanding activity. Data is transmitted the exercise demand phase. The Subject is instructed to stop and a recovery measurement is made by all the MCO biosensors. Greater variability from non-exercise to intense exercise oxygen levels is associated with MCO-S. This data is transmitted to the descriptive and performance data tables. This is variability activity 1 or V-1

The subject is instructed in a deep breathing exercise. Deep breathing increase oxygen variability and is associated with strong MCO-S. The data is transmitted to the descriptive and performance data tables. This is variability activity two or V-2

The subject is instructed in a brain wave training program which measure the Theta/beta ratio wherein the subject's goals is to lower the ratio. This activity is correlated with attention and concentration and shows greater variability in strong MCO-S subjects. The data is transmitted to the descriptive and performance data tables. This is variability activity three or V-3

The subject is instructed in a brain wave training with an Alpha/Theta program. This activity is correlated with working memory and is correlated with MCO-S. The data is transmitted to the descriptive and performance data tables. This is variability activity three or V-4

The subject is instructed in a brain wave training with an Alpha wave enhancement program. This activity is correlated with problem solving and is correlated with MCO-S. The data is transmitted to the descriptive and performance data tables. This is variability activity three or V-5

The subject is instructed in a brain wave training with an Alpha wave phase coherence enhancement program. This activity is correlated with pattern recognition and is correlated with MCO-S. The data is transmitted to the descriptive and performance data tables. This is variability activity three or V-6

The subject is asked to provide a structure voice tract. Voice patterns correlated with stress and lower stress level are associated with MCO Network strength. This is variability activity three or V-7

Therefore, the MCO Network Strength is MCO-SA.-MCO-DA+V1+V2+V3+V4+V5+V6+V7. This algorithm is enhanced with comparison to the system descriptive and performance data tables.

The System AI engine rank orders the patterns by way of ordinal levels and permutation change metrics. The permutation change metric is a measurement of the optimal permutation changes among the V2 through V6 activities. Greater maximum and number of areas are correlated with MCO Network strength.

The MCO Network Strength App can be integrated with a Virtual Reality immersive environment. This integration creates a novel assessment process. The MCO Network Strength App can integrate the MCO-SA, MCO-DA and V1 through V7 with immersive images of representing the user's heart, (HRV rhythms), oxygen (Aortic color changes) and brain wave resonance of brain structures to create a novel measurement called a Correspondence Virtual Reality measurement. This can be used in the MCO Assessment process by having the user view his CRV images while the assessment process is being administered.

The MCO Network Strength App can also be integrated with a Virtual Reality immersive environment for real time intentional imaging as stated above but also near real time images (i.e. drug administration) and long-term image changes and variance from normal (i.e. Alcohol Use images). Both processes are aimed at developing long term insight and education into the effects of external stimuli on the near- and long-term functions of the MCO Network Strength. This application is aimed at health and wellness education as well as a general learning tool.

The current invention can, in addition to a smart phone device, be used with a Virtual Reality system. In this case the subject is viewing an immersive 3D image of the effect of the assessment process on the various internal organs being assessed, in the case of MCO Network Strength Assessment these would be immersive 3d Images of the subject brain, aortic system and heart rate functions. The immersive images are also being affected by the MCO system real time data streams. This creates a novel type of MCO Network Assessment based on a Correspondent Virtual Reality image. A Correspondent Virtual Reality immersive 3D image is a classical VR Image that is being modified in real time, near real time or long term changing with an MCO data stream for the purpose of optimization of the MCO Network Strength.

In one implementation, the assessment proceeds as follows:
1. The MCO Resting State Network Assessment will be a 10 min test
2. It will be driven by smart phone directed instructions
3. The initial data will be put into data fields based on the RSS Algorithm
4. This is composed of the following
   a. An Eyes Closed resting state measurement 30 sec
   b. A reflexive eye open instantaneous measurement (not task dependent) 30 sec
   c. An intentional Theta/Beta Measurement (concentration) 3 min
   d. An intentional Alpha Percentage measurement (problem solving) 3 min
   e. An Intentional Phase Coherence Measurement (pattern recognition) 3 min
5. An MCO/RSS automatic report is generated within a minute or less.
6. The report provides a measurement of a set of subtests and an overall MCO Resting State Strength Measurement all on a scale of 1-200 with 100 being average.
7. The reported measurements will be
   a. Eye Closed subtest scale 1-200
   b. Differential State scale (eyes open) 1-200
   c. Concentration Capacity 1-200
   d. Problem Solving Capacity 1-200
   e. Pattern Recognition Capacity 1-200
   f. Full Scale Resting State Strength 1-200
      i. MCO/RSS=EO−ECdelta+Theta/Beta+IApercent+IAlphaPhaseCoherence/Physcial Age×100

RSS is developed in a similar manner as an IQ test and other psychometric tests.

Brain wave data is age dependent; that is, the normative data changes with age.

Normative Data must to be considered in the context of age. Normative gaussian features of age-related brain wave data has been established in the brain wave eyes closed normative data bases by Dr. R. Thatcher, Dr. E R John and Dr. F Duffy. These have been replicated using fMRI Resting State Network data.

IQ Scores are also calculated based on age.

The mental age score is achieved by the individual being compared to the median average scores at various ages, and the mental age (x, say) is derived such that the individual's score equates to the average score at age x.

$$IQ = \text{Mental age} \div \text{Physical age} \times 100 \quad \text{a.}$$

The MCO Resting State Network Strength score achieved by the individual being compared to the median average "MCO RSS Age Pattern Data Packet at various ages, and the MCO RSS Age Pattern Data Packet Score (x, say) is derived such that the individual's MCO RSS Age Pattern Data Packet Score equates to the average score at age x.

$$RSS = \text{MCO RSS Age Pattern Data Packet Score} / \text{Physical Age} \times 100$$

Figure 8:
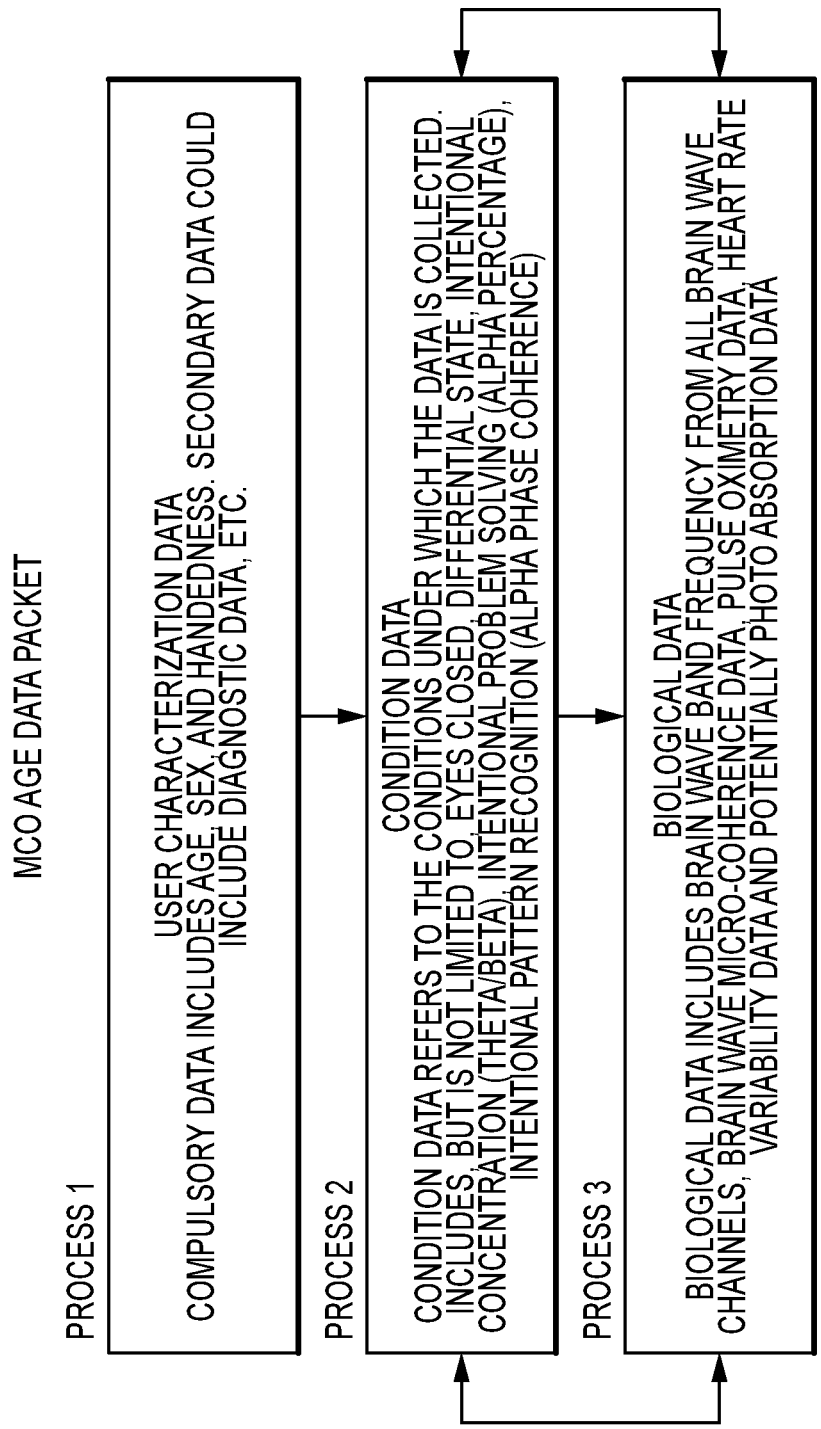
FIG. 8 is a diagram of an age data packet in accordance with the present invention.

The MCO Age Patterns Data packet is composed of three different forms of data as shown in FIG. 8, These are
1. Condition Data. Condition data refers to the conditions under which the data is collected. That is eyes open, differential state, Intentional Concentration (Theta/Beta), Intentional Problem solving (Alpha Percentage) Intentional Pattern Recognition (Alpha Phase Coherence).
2. User Characterization Data. Compulsory data includes age, sex and handedness. Secondary data could include diagnostic data etc.
3. Biological Data. Biological data includes brain wave band frequency from all brain wave channels, brain wave micro-coherence data between all brain wave electrodes, pulse oximetry data, heart rate variability data and potentially photon absorption data.

In the preferred embodiment biological data would be collected in the background of all conditions. However, information on data stream management is needed here.

The MCO Resting State Network Strength score is advanced by an increasingly large number of subjects through the cold start and commercial process.

All the above data is optimized using the IP App Subroutine smart phone programs.

Deep Behavior Modification

The current invention is aimed at combining a Micro-Coherence Oximetry (MCO) Forehead Sensor composed of two EEG sensors and related Reflectance Oximetry measurement, to provide for an initial calculation of a combined integrated measurement of micro brain wave coherence, frequency and high-resolution pulse oximetry data and from this data calculate a Micro-Resting State Network activation and deactivation difference. In addition, intentional variability and cognitive training data is integrated through the system data tables to calculate a Micro Resting State Network strength index.

Figure 9:
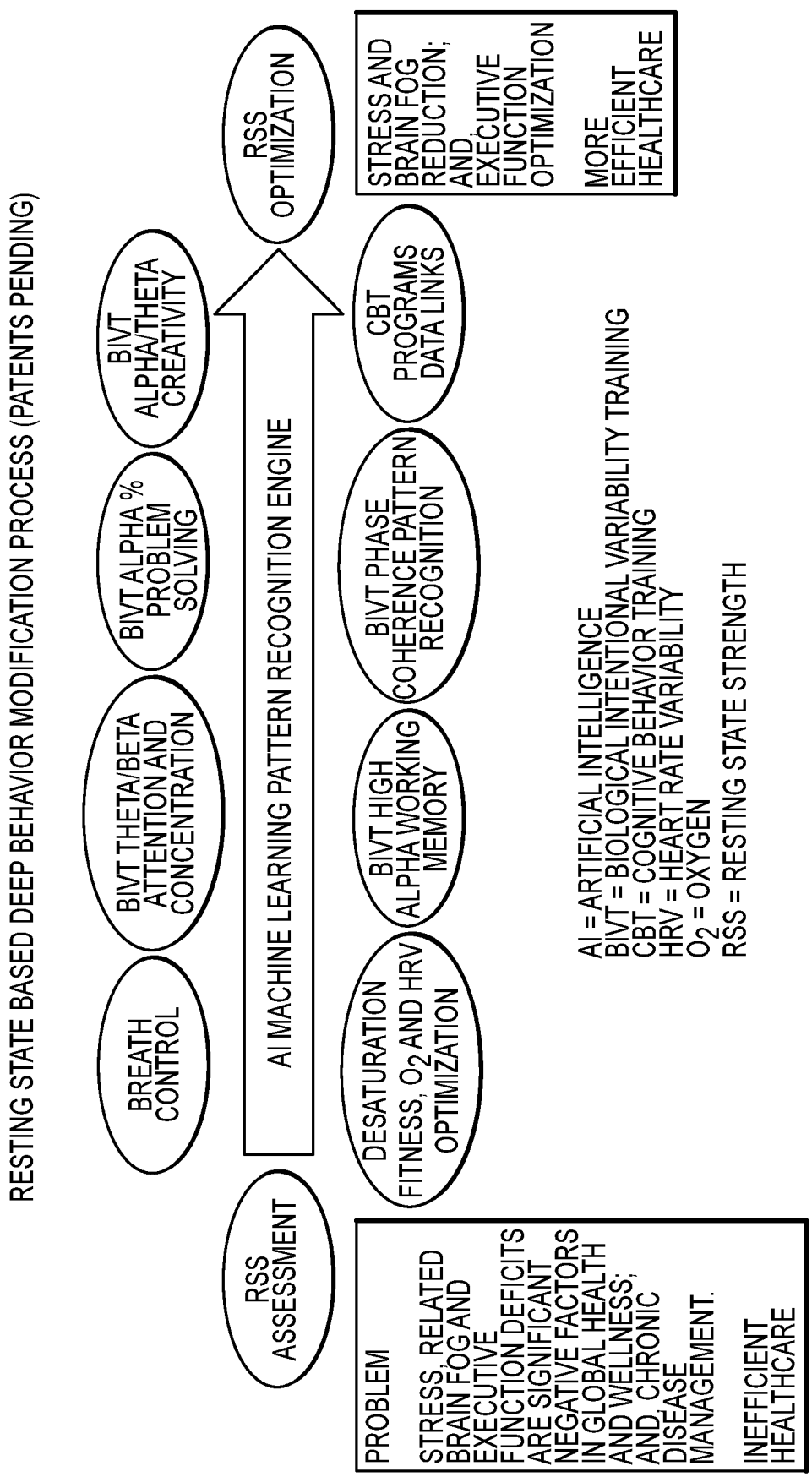
FIG. 9 is a diagram of a resting state based deep behavior modification process in accordance with the present invention.

Furthermore, the application uses this Micro-Resting State Network Strength measurement to guide a Deep Behavior Modification programing system in breath control, precision interval exercise, self-regulation brain wave program and cognitive behavior training program as generally illustrated in FIG. 9. Deep Behavior Modification is the integration of artificial intelligence (machine learning) directed self-regulation programs in breath control, interval fitness and direct brain wave regulation, combined with cognitive and behavioral restructuring programs on the user's smart phone; all intended for stress management, brain fog reduction and executive function optimization, and to enhance peer to peer Micro-Resting State Network communication.

The Application processes the MCO-S data through a novel pattern recognition process that is enhanced by various standard and customized AI functions and Deep Machine Learning processes. This novel pattern recognition system is composed of five modules. These are an averaging model by subject age, a likes module, a permutation change module, a successive approximation model ((slope and threshold analysis) and a Deep Machine Learning module aimed at detecting deep optimization pattern within the prior three modules.

The pattern recognition module receives data from two primary data tables. These are a Descriptive data table and a Performance data table. The data sets are also optimized using unstructured (commercial data) and structured (experimental data).

In addition, the Micro Coherence Oximetry Network based Deep Behavior Modification Application obtains a novel measurement of the MCO Network Strength of the human nervous system through a forehead band that measures 4 brain wave channels, one pulse oximetry (used for HRV as well) channel and one or more Galvanic Skin conductance channels One intended use of the system is to optimize a complex of interrelated data for the purpose of the user optimization the MCO Network using the system's IVT and CBT programs. IVT programs are fitness (desaturation) programs, breath control programs a various cognitively correlated self-regulation brain wave programs. CBT programs are Cognitive Behavior Training or sometimes call Therapy program that are aimed at optimizing the users thought and actions around general health and wellness, surgical recovery and/or chronic disease management.

This creates very large interactive data sets wherein the optimizing choice of sets and settings relative to the IVT and CBT, descriptive and performance data as well as structure and unstructured data need to be found using an AI machine learning program.

In order to find and optimize set and setting configurations on the user's smart phone or VR system the Application uses a novel pattern recognition algorithm which interacts with the data tables. The initial IVT setting include but are not limited to:
1. Time duration per training session
2. Permutation Change Calculation
3. Frequency of training sessions per day, week, month, year
4. Overall activity sequence 6
5. Programmed learning Intentional Variability Training (IVT) integrated successive approximation system for IVT learning optimization
6. Resting state trigger shaping schedule
7. Environmental status checks: stress, food/exercise, food pattern analytics
8. Resting State Strength prompts
9. Reinforcement types and schedules
10. Compliance shaping system
11. Cognitive Training Programing Personal
12. Cognitive Therapy program Practitioners
13. Sets interval and intensity load for the next physical exercise
14. Set out a 3-day set of programs settings=4896 Possibilities then redo RSS.
15. Recovery Periods during interval exercise training.

The novel pattern recognition system works in the following way.

This data is initially structured according to the Micro-Coherence Network Strength Application protocol. This protocol provides the data input to the Deep Behavior Modification AI pattern recognition engine This data is then structured into two modules by the Age normative module of the system's AI engine. This initial data structure is used to set up three IVT programs and to select one or more preliminary Cognitive Behavior Training programs on the user's smart phone.

The IVT programs are of three types. These are breath regulation programs, interval fitness programs and various brain wave training programs. The objective of the breath control programs is to teach the user how to increase oxygen variability using the Pulse Oximetry data and HRV signals as guiding feedback. This training also changes the brain wave of the user to become more variable.

The interval fitness program is aimed at using a heart rate guided program to increase exercise intensity so that the user's oxygen desaturation levels are lower thus expanding the variability of the user's oxygen capacity. This program also increases the variability of the user's heart rate variability and various brain wave patterns. All data is collected both during intensity activities (to degree possible with Noise cancellation) and most importantly during short period of recovery.

The brain wave training programs are to four distinctive types. The self-regulation training program are aimed at overall brain wave variability increases and also targeted to specific patterns that are correlated to cognitive and emotional wellbeing. These brain wave programs are. 1. A Theta/Beta program for attention and concentration. 2. an Alpha/Theta program for working memory and 3 an Alpha frequency increase for problem solving, and 4 an Alpha Phase coherence program for pattern recognition improvements.

The initial set up also selects one or more Cognitive Training programs from a library of Cognitive Training Programs. These Cognitive Behavior Training contain various cognitive training techniques within areas of interest for the user or techniques around cognitive training with respect to diseases or conditions.

The Deep Behavior Modification pattern recognition engine is composed of five patterns recognition modules and three support tales. The five-pattern recognition modules are: (1) a module of age-related averages, (2) a module of user "Likes" ratings of various IVT and CBT set ups and program selection, (3) a permutation change calculator module. This module is intended to allow the AI engine to search the user's data and similar user's data to find the optimal permutation of training activities and settings which represent the most effective variables for MCO network optimization. The permutation change represents the most powerful set of training activities and setting that will strengthen the MCO Network and thus will be prioritized in the smart phone or CVR system. (4) a successive approximation module. This module provides an analysis of the best threshold settings by way of percentage threshold achieved and provides a detailed analysis of the solve functions for each threshold and other setting to determine the optimal learning solution for each threshold and function. (5) this module is a Deep Machine Learning module aimed at finding the optimal path through the preceding three modules in order to optimize the user's compliance and learning of the IVT and CBT program goals.

The AI Engine information system is augmented with four additional type of data tables. These are descriptive data tables, performance data tables, tables of commercial data relatively unstructured and structured data tables from various controlled scientific studies.

All data is synthesized in the AI engine to provide the maximum set and setting for the Smart phone.

The Micro Coherence Oximetry Network based Deep Behavior Modification Application is also intended to be integrated with Virtual Reality (VR) systems. The integration of the Micro Coherence Oximetry Network based Deep Behavior Modification Application with VR creates a novel set of immersive imaging. The VR System can create immersive images of the human heart, aortic blood flow and brain structures particularly the Amygdala among others so that the user's perceptual field is sufficient modified to perceive this image living system. These images will be integrated with real time data stream from the MCO head band, assessment data structure and IVT and CBT Deep Behavior Modification processes, creating a new data reality within this application is called Correspondence Virtual Reality.

Correspondence Virtual Reality is the integration of real time MCO data stream (or non MCO Data Streams) with immersive images of the bodily organs being impacted by the intentional process or some type of near real time or long-term stimuli. The purpose of this MCO Deep Behavior Modification data streams is to change the perceptual field of the IVT and CBT program effects on the bodily organs to enhance optimization of the human nervous system Micro Coherence Network and for transmission to an AI machine learning engine also for optimization of the human nervous system Micro Coherence Network.

With respect to non-real time data, its purpose is also to enable optimization of the human nervous system Micro Coherence Network and for transmission to an AI machine learning engine also for optimization of the human nervous system Micro Coherence Network through knowledge and insight development.

The MCO Network Strength App can be integrated with a Virtual Reality immersive environment. This integration creates a novel assessment process. The MCO Network Strength App can integrate the MCO-SA, MCO-DA and V1 through V7 with immersive images of representing the user's heart, (HRV rhythms), oxygen (Aortic color changes) and brain wave resonance of brain structures to create a novel measurement call a Correspondence Virtual Reality measurement. This can be used in the MCO Assessment process by have the user view his CRV images while the assessment process is being administered.

Fitness and Health Assessment and Optimization

The Micro-Resting State Network Strength MCO-S application is aimed at assessing the strength of the human Micro-Coherence Network Strength before and after exercise effects. The measurement is initiated by the collection of data from various bio sensors on the human forehead that measure brain waves, pulse oximetry, heart rate variability and galvanic skin conductance.

The application performs this measurement by way of measuring the Micro-Coherence Network Strength Activation and Deactivation differences with or without combining this measurement with a biological intentional variability measurement, scaling the measurement for total strength measurement and then translating this assessment into a numeric scale or Virtual Realty immersive experience.

The MCO-S Network is a measurement that is a corresponding measurement of the human nervous system Default Mode Network. The Default Mode Network is a reflex network that is triggered when a person closes their eyes and "rests". It is also known as the Resting State Network. It is an overall nervous system network that has been measured using brain EEG measurements, neuroimaging measurements including fMRI, PET and magnetoencephalography. It has also been measured using Heart Rate Variability and Galvanic Skin conductance. It can be triggered as a reflex by all human beings as it is a reflex and does not require a mindful effort or training and is independent of the subject's knowledge level.

The MCO-S measurement is compared to a set of two types of data tables. These are descriptive data tables and performance data tables. Each table has an initiating data cell for age related averages of the activation and deactivation with or without intentional variability data. The descriptive data tables provide for various descriptive categories in application focused on exercise and fitness. The performance data tables provide for, intentional variability data, cognitive restructuring data and voice pattern analysis data all correlated to exercise and fitness.

The Intentional Variability metric is based on a set of intentional behavior modification exercise measurements in breath control, precision exercise intervals, and self-regulated brain wave exercises. The system calculates a table of permutation change patterns related to the intentional variability exercises and ranks them with respect to age, descriptive and performance characteristic.

The cognitive behavior training metric is derived from various cognitive behavior training data often collected on the subject's smart phone or VR device focused on Fitness Assessment and Exercise Optimization.

Furthermore, the application uses this Micro-Resting State Network Strength measurement to guide an MCO Network Strength exercise optimization programing system in breath control, precision interval exercise, self-regulation brain wave program and cognitive behavior training program. It will be linked to a large library of exercise programs and exercise and fitness equipment that provide data for the descriptive and performance data tables.

An MCO Network Strength optimization exercise program is the integration of artificial intelligence (machine learning) directed self-regulation programs in breath control, interval fitness and direct brain wave regulation, combined with cognitive and behavioral restructuring programs all on the user's smart phone or Virtual Reality Device, all intended for quantifying and optimization an exercise program.

The Application processes the MCO Network Assessment data through a novel pattern recognition process that is enhanced by various standard and customized AI functions and Deep Machine Learning processes. This novel pattern recognition system is composed of five modules. These are an averaging model by subject age, a "likes" module, a permutation change module, a successive approximation model (slope and threshold analysis) and a Deep Machine Learning module aimed at detecting deep optimization pattern within the prior three modules.

The pattern recognition module receives data from two primary data tables these are a Descriptive data table and a Performance data table. The data sets are also optimized using unstructured (commercial data) and structured (experimental data).

The MCO Network Assessment and Fitness Application uses this Micro-Resting State Network Strength measurement to guide the Fitness programing system in breath control, precision interval exercise, self-regulation brain wave program and cognitive behavior training program. An MCO Network Strength Fitness program is the integration of artificial intelligence (machine learning) directed self-regulation programs in breath control, interval fitness and direct brain wave regulation, combined with cognitive and behavioral restructuring programs all on the user's smart phone. All intended to link fitness programing to human nervous system optimization especially the MCO Network Strength.

The Application processes the MCO-S data through a novel pattern recognition process that is enhanced by various standard and customized AI functions and MCO Fitness Assessment and Optimization processes. This novel pattern recognition system is composed of five modules. These are an averaging model by subject age, a likes module, a permutation change module, a successive approximation model (slope and threshold analysis).) and a Deep Machine Learning module aimed at detecting deep optimization pattern within the prior three modules.

The Micro Coherence Oximetry Network based MCO Fitness Assessment and Optimization App obtains a novel measurement of the MCO Network Strength of the human nervous system through a forehead band that measures 4 brain wave channels, one pulse oximetry (used for HRV as well) channel and one or more Galvanic Skin conductance channels One intended use of the system is to optimize a complex of interrelated data for the purpose of the user optimization the MCO Network using the system's IVT and CBT programs. IVT programs are fitness (desaturation) programs, breath control programs a various cognitively correlated self-regulation brain wave programs. CBT programs are Cognitive Behavior Training or sometimes call Therapy programs that are aimed at optimizing their users thought and actions around general health and wellness, surgical recover and/or chronic disease management.

This creates very large interactive data sets wherein the optimizing choice of sets and settings relative to the IVT and CBT, descriptive and performance data as well as structure and unstructured data need to be found using an AI machine learning program.

In order to find an optimize set and setting configuration on the user's smart phone or VR system the Application uses a novel pattern recognition algorithm which interacts with the data tables. The initial IVT setting include but are not limited to:

1. Time duration per training session
2. Permutation Change Calculation
3. Frequency of training sessions per day, week, month, year
4. Overall activity sequence 6
5. Programmed learning Intentional Variability Training (IVT) integrated successive approximation system for IVT learning optimization
6. Resting state trigger shaping schedule
7. Environmental status checks: stress, food/exercise, food pattern analytics
8. Resting State Strength prompts
9. Reinforcement types and schedules
10. Compliance shaping system
11. Cognitive Training Programing Personal
12. Cognitive Therapy program Practitioners
13. Sets interval and intensity load for the next physical exercise
14. Set out a 3-day set of programs settings=4896 Possibilities then redo RSS.
15. Recovery Periods during interval exercise training.

The novel pattern recognition system works in the following way.

This data is initially structured according to the Micro-Coherence Network Strength Application protocol. This protocol provides the data input to the MCO Fitness Assessment and Optimization App AI pattern recognition engine This data is then structured into two modules by the Age normative module of the system's AI engine. This initial data structure is used to set up three IVT programs and to select one or more preliminary Cognitive Behavior Training programs on the user's smart phone.

The IVT programs are of three types. These are breath regulation programs, interval fitness programs and various brain wave training programs. The objective of the breath control programs is to teach the user how to increase oxygen variability using the Pulse Oximetry data and HRV signals as guiding feedback. This training also changes the brain wave of the user to become more variable.

The interval fitness program is aimed at using a heart rate guided program to increase exercise intensity so that the user's oxygen desaturation levels are lower thus expanding the variability of the user's oxygen capacity. This program also increases the variability of the user's heart rate variability and various brain wave patterns. All data is collected both during exercise intensity activities (to degree possible with Nosie cancellation) and most importantly during short period of recovery.

The brain wave training programs are to four distinctive types. The self-regulation training program are aimed at overall brain wave variability increases and also targeted to specific patterns that are correlated to cognitive and emotional wellbeing. These brain wave programs are. 1. A Theta/Beta program for attention and concentration. 2. an Alpha/Theta program for working memory and 3 an Alpha frequency increase for problem solving, and 4 an Alpha Phase coherence program for pattern recognition improvements.

The initial set up also selects one or more Cognitive Training programs from a library of Cognitive Training Programs. These Cognitive Behavior Training contain various cognitive training techniques within areas of interest for the user or techniques around cognitive training with respect to diseases or conditions.

The MCO Fitness and Optimization App pattern recognition engine is composed of five patterns recognition modules and three support tales. The five-pattern recognition modules are a (1) module of age-related averages, (2) a module of user "Likes" ratings of various IVT and CBT set ups and program selection, (3) a permutation change calculator module. This module is intended to allow the AI engine to search the user's data and similar user's data to find the optimal permutation of training activities and setting which represent the most variability. The permutation represents the most powerful set of training activities and setting that will strengthen the MCO Network and thus will be prioritize in the smart phone or CVR system. (4) a successive approximation module. This module provides and analyst of the best threshold setting by way of percentage threshold achieved and provides a detailed analysis of the solve functions for each threshold and other setting to determine the optimal learning solve for each threshold and function. (5) this module is a Deep Machine Learning model aimed at finding the optimal path through the preceding three modules in order to optimize the user's compliance and learning of the IVT and CBT program goals.

The AI Engine information system is augmented with four additional type of data tables. These are descriptive data tables, performance data tables, tables of commercial data relatively unstructured and structured data tables from various controlled scientific studies.

All data is synthesizing in the AI engine to provide the maximum set and setting for the Smart phone.

The Micro Coherence Oximetry Network based MCO Fitness and Optimization App is also intended to be integrated with Virtual Reality (VR) systems. The integration of the Micro Coherence Oximetry Network based Deep Behavior Modification Application with VR creates a novel set of immersive imaging. The VR System can create immersive images of the human heart, aortic blood flow and brain structures particularly the Amygdala among others so that the user's perceptual field is sufficient modified to perceive this image a living organ. These images will be integrated with Real time data stream from the MCO head band, assessment data structure and IVT and CBT Deep Behavior Modification process creating a new data reality within this application is called Correspondence Virtual Reality.

Correspondence Virtual Reality is the integration of real time MCO data stream (or non MCO Data Streams) with immersive images of the bodily organs being impacted by the intentional process or some type of near real time or long-term stimuli. The purpose of this MCO Fitness and Optimizations App data streams is to change the perceptual field of the IVT and CBT program effects on the bodily organs to improve optimization of the human nervous system Micro Coherence Network and for transmission to an AI machine learning engine also for optimization of the human nervous system Micro Coherence Network.

With respect to non-real time data is purpose is also to improve optimization of the human nervous system Micro Coherence Network and for transmission to an AI machine learning engine also for optimization of the human nervous system Micro Coherence Network through knowledge and insight development.

The foregoing description of the present invention has been presented for the purpose of illustration and description. Furthermore, the description is not intended to limit the invention to the form disclosed herein. Consequently, variations and modifications commensurate with the above teachings, and skill and knowledge of the relevant art are within the scope of the present invention. The embodiments described herein above are further intended to explain best modes known of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed:

1. A method for use in monitoring a subject, comprising:
providing a sensor device including one or more external sensors, disposed external to said subject, for sensing signals indicative of at least one of subject brainwaves, heart rate variability and galvanic skin conductance;
first applying said sensor device to said subject to obtain first measurements of said signals when said subject is in at least one of first and second states that are part of a first, predefined regimen of intentional focused exercises, wherein each of said first and second states has a known correlation to a biological substrate, said biological substrate comprising a set of physiologic parameters and physiologic parameter values indicative of a status in relation to a defined health and wellness objective;

performing an assessment of said subject with respect to said status in relation to said defined health and wellness objective based at least in part on said first measurements;

based on said assessment, developing a set of behavior modification exercises for said subject to address said health and wellness objective;

second applying said sensor device to said subject to obtain second measurements of said signals when said subject is engaged in said behavior modification exercises; and in connection with said behavior modification exercises, providing real-time feedback information to said subject concerning said second measurements so that said subject can self-regulate Default Mode Network behavior in relation to performance of said behavior modification exercises to alter said second measurements and optimize said status in relation to said defined health and wellness objective.

2. The method of claim 1, wherein said sensors include pulse oximetry sensors.

3. The method of claim 2, wherein an output from said oximetry sensors is processed to obtain heart rate variability information.

4. The method of claim 1, wherein said sensors include EEG sensors.

5. The method of claim 4, wherein an output from said EEG sensors is used to obtain information regarding one of a brainwave Theta-Beta ratio, a brainwave Alpha wave, and brainwave Alpha wave coherence.

6. The method of claim 1, wherein said first state involves having the subject close his eyes, and said first measurements are obtained when said subject is in said first state.

7. The method of claim 1, wherein said second state involves having the subject open his eyes, and said first measurements are obtained in said second state.

8. The method of claim 1, wherein said first and second states involve having the patient close and open his eyes, respectively, and said first measurements are obtained in each of said first and second states.

9. The method of claim 8, further comprising using said measurements for said first and second states to obtain a strength value related to a Default Mode Network of said subject.

10. The method of claim 1, further comprising assessing a variability related to a Default Mode Network of said subject.

11. The method of claim 10, wherein said assessing comprises obtaining measurements from said sensor device in connection with one or more intentional variability training (IVT) exercises performed by said subject.

12. The method of claim 11, wherein said IVT exercises include performing an activity to induce a blood oxygen desaturation event.

13. The method of claim 11, wherein said IVT exercises include a deep breathing exercise.

14. The method of claim 11, wherein said IVT exercises include obtaining said measurements in connection with a state of mental concentration of said subject.

15. The method of claim 11, wherein said IVT exercises include obtaining said measurements in connection with a state of problem solving of said subject.

16. The method of claim 11, wherein said IVT exercises include obtaining said measurements in connection with a state of active pattern recognition of said subject.

17. The method of claim 11, wherein said IVT exercises include providing a voice track of said subject.

18. The method of claim 11, further comprising obtaining measurements in connection with multiple ones of said IVT exercises and combining information from said measurements to obtain assessment information related to a Default Mode Network of said patient.

19. The method of claim 18, using said assessment information to develop an optimization protocol for optimizing a Default Mode Network of said patient.

20. The method of claim 19, wherein said optimization protocol is developed by employing a processing system to determine at least a selected set of Default Mode Network exercises and a set of parameters for executing said exercises.

21. The method of claim 20, wherein said processing system implements machine learning to progressively optimize said Default Mode Network in relation to said defined health and wellness objective.

22. The method of claim 19, wherein said optimization protocol is directed to optimize an objective related to one of fitness and athletic performance.

23. The method of claim 19, wherein said optimization protocol is directed to optimize an objective related to one of reducing mental fog and increasing concentration.

24. The method of claim 19, wherein said optimization protocol is directed to optimize an objective related to managing stress levels.

* * * * *